US006472150B1

(12) United States Patent
Killeen et al.

(10) Patent No.: US 6,472,150 B1
(45) Date of Patent: Oct. 29, 2002

(54) SIFTER SCREENING TO IDENTIFY BIOLOGICALLY ACTIVE MOLECULES

(75) Inventors: Gerry F. Killeen, New Orleans, LA (US); Brian D. Fox, New Orleans, LA (US); John C. Beier, Folsom, LA (US)

(73) Assignee: Administators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 09/359,918

(22) Filed: Jul. 22, 1999

Related U.S. Application Data (60) Provisional application No. 60/094,036, filed on Jul. 24, 1998, now abandoned.

(51) Int. Cl.[7] .......................... C12Q 1/70; C12N 15/00; C07K 16/00; C07H 21/02
(52) U.S. Cl. ........................... 435/6; 435/320.1; 435/5; 435/DIG. 1; 435/DIG. 2; 435/DIG. 3; 435/DIG. 4; 435/DIG. 14; 435/DIG. 34; 436/518; 530/300; 530/387.1; 530/388.1; 536/23.1

(58) Field of Search ...................... 435/7.1, 6.5, 235.1, 435/320.1, DIG. 1, DIG. 2, DIG. 3, DIG. 4, DIG. 14, DIG. 34; 530/300, 387.1, 388.1; 436/518; 536/23.1

(56) References Cited

PUBLICATIONS

Beier et al., Ann. Rev. Entamology, 1998, vol. 43: 519–43.*

* cited by examiner

*Primary Examiner*—Padmashri Ponnaluri
(74) *Attorney, Agent, or Firm*—Benjamin Aaron Adler (57) ABSTRACT

A novel single-insect feeding, testing and recovery (SIFTER) strategy is described for screening and isolating biomolecules that exert a desired biological activity in arthropods, preferably insects. Biomolecules are screened for desirable activity by feeding a population of arthropods an array of biomolecules and subsequently recovering the biomolecule(s) from detectably affected individuals.

14 Claims, 5 Drawing Sheets

SIFTER SCREENING TO IDENTIFY BIOLOGICALLY ACTIVE MOLECULES

CROSS-REFERENCE TO RELATED APPLICATIONS

This application claims the benefit of priority under 35 USC §119(e) of provisional application U.S. Ser. No. 60/094,036 filed Jul. 24, 1998, now abandoned.

FEDERAL FUNDING LEGEND

This invention was produced in part using funds obtained through grant R01-AI29000 from the National Institutes of Health. Consequently, the federal government has certain rights in this invention.

BACKGROUND OF THE INVENTION

1. Field of the Invention

The present invention relates generally to the field of biology. More specifically, the present invention relates to methods of screening for biologically active molecules against arthropods or biologically active molecules that effectively reduce the ability of vector arthropods to transmit their respective pathogen(s).

2. Description of the Related Art

Biomolecules which either directly kill arthropods or reduce their capacity to transmit pathogens have many potential applications. Examples include plant protection from pests by microbial insecticides (Stewart et al., 1996) and the development of vaccines to block the transmission of pathogens or to directly kill their vectors (Billingsley, 1994, Jacobs-Lorena & Lemos, 1995, Willadsen & Billingsley, 1996, Almeida & Billingsley, 1998). The search is ongoing for new (Bowen et al., 1998) and modified (Marzari et al., 1997,. Kasman et al., 1998) biopesticide molecules, as well as genes which cause insect refractoriness to pathogens (Marshall, 1998) and leads to vaccines against blood-feeding arthropods (Billingsley, 1994, Jacobs-Lorena & Lemos, 1995, Willadsen & Billingsley, 1996, Almeida & Billingsley, 1998). However, the laborious process of identifying genes and gene products in recombinant libraries which have in vivo biological activities often limits the progress of such investigations (King et al., 1997).

High-diversity, phage-display expression libraries readily allow the isolation of high affinity human antibody fragments against almost any antigen without any immunization step (Vaughan et al., 1996, Vaughan et al., 1998). Phage display libraries are also capable of generating panels of antibody fragments with wide specificities for different antigens in complex mixtures (Cai & Garen, 1995) and have been recognized as promising tools for the development of anti-vector vaccines (Willadsen & Billingsley, 1996). Furthermore, phage-display libraries are propagated in the common recombinant host *Escherichia coli*, which is also the most commonly found bacterium in wild *A. gambiae* and *A. funestus* (Straif et al., 1998). Existing phage-display recombinant antibody expression systems therefore represent a convenient system for the delivery of recombinant proteins or peptides, and the phagemids which encode them, to the midgut of these important malaria vectors.

The prior art is deficient in effective methods of screening for biomolecules that either kill or reduce the longevity of an arthropod and for biomolecules which reduce or completely inhibit an arthropod's ability to act as a host vector for a pathogen. The present invention fulfills this long-standing need and desire in the art.

SUMMARY OF THE INVENTION

A novel single-insect feeding, testing and recovery (SIFTER) strategy is described for isolating biomolecules (e.g., clones from nucleic acid libraries), wherein the biomolecules exert a desired biological activity in arthropods (e.g., insects). Theoretically, biomolecules causing desired phenotypes in arthropods may be isolated by allowing groups of arthropods to feed on arrays of single biomolecules and recovering active biomolecules from detectably affected individuals.

A model has been developed, and is described herein, in which arrays of single clones from a library of antibody gene constructs were fed to cages of *Anopheles gambiae* mosquitoes. Clones were fed as a combination of expressed antibody fragments and bacteria containing the phagemids which encode these fragments. The model screening system reduced the burden of rigorously testing individual clones by up to 125-fold.

The SIFTER strategy has applications which go beyond the described model, including screening for clones which kill arthropods or reduce their competence as disease vectors, thereby leading to biopesticides and vaccines for the control of vector-borne diseases. It is proposed that the principles of SIFTER are applicable to screening any library for biological activity in arthropods and/or insects, if the following criteria can be fulfilled: a) individuals sample the arrays representatively and each individual samples only one clone; b) clones are recoverable from the individual; c) desired activities are readily and rapidly identifiable; and d) background levels of false positives for the activity are low.

One object of the present invention is to provide a method of screening, termed single-insect feeding, testing and recovery, for biologically active molecules directed towards arthropods, preferably insects, even more preferably, mosquitoes.

In an embodiment of the present invention, there is provided a method of screening for a biologically active molecule directed towards a species of arthropod, comprising the steps of: (a) feeding an array of elements, each of which contains a different biomolecule or mixture of biomolecules, to a population of a species of arthropod, wherein individual arthropods preferably feed on a single element but has the opportunity to feed upon any element in the array; (b) testing said arthropods for a desired phenotype, wherein said desired phenotype is indicative of one or more biomolecules, aquired by feeding from an element of the array, possessing biological activity towards said species of arthropod; and (c) recovering biomolecule(s) resulting in said desired phenotype from said arthropods displaying said desired phenotype.

In yet another embodiment of the present invention, there is provided a method of screening for a biologically active molecule directed towards the malaria vector mosquito, *Anopheles gambiae*, comprising the steps of: (a) feeding an array of biomolecules to a population of *Anopheles gambiae*, wherein individual *Anopheles gambiae* preferably feed on a single biomolecule; (b) testing said *Anopheles gambiae* for a desired phenotype, wherein said desired phenotype is indicative of one or more biomolecules possessing biological activity towards said *Anopheles gambiae*; and (c) recovering said biomolecule(s) resulting in said desired phenotype from the midgut of said *Anopheles gambiae* displaying said desired phenotype.

Additionally, the above-described methods may further comprise the step of: performing iterative cycles of steps (a), (b) and (c) until the biomolecule(s) are purified. The aboveembodied methods may still further comprise the step of: enriching the array of biomolecules for midgut-specific biomolecules prior to the feeding.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 2A: Mosquitoes feeding on an array of periplasmic extracts midgut-selected clones mixed with blood in a microtiter plate. FIG. 2B: The pattern of pre-diuresis fluid (serum and lysed red blood cell contents excreted during the blood-feeding) on filter paper directly under the array on the bottom of the cage. FIG. 2C: Detection, by dot-blot, of antibody fragments in individual mosquitoes following feeding from the 96-clone array of scFv-containing periplasmic extracts. Antibody fragments were separately extracted from the midgut (MG) and remaining carcass (CA). Extracts from mosquitoes fed identical preparations from pCANTAB-6 (phagemid lacking scFv insert) are shown as a control.

FIG. 3A: Bacterial colonies recovered from blood meals and midgut contents at various times before (0 hr) and after (24–72 hr) feeding to *Anopheles gambiae* of either scFv and bacteria from the high-producing anti-FITC-E2 clone (scFv clone) or extraction buffer alone (control). FIG. 3B: Dot-blotted antibody fragments from clones recovered from mosquitoes fed on a 96-clone array. Clones from phage-packaged phagemids which were individually recovered from each of twelve dead mosquitoes. These were re-infected into fresh HB2151 and induced to produce scFv which was subsequently detected in host cells by dot blot and compared to the construct alone (pCANTAB-6).

FIG. 4 shows the tailoring of SIFTER conditions to minimize false positives during screens for *Anopheles gambiae*-killing clones. Escherichia coli with pCANTAB-6 phagemid alone was grown under inducing conditions and its periplasm extracted, mixed with blood and presented to *A. gambiae*, after which time feeding rates (FIGS. 4A and 4C) and 24 hour post-feeding mortality numbers (FIGS. 4B and 4D) were recorded. The influence of the ratio of blood to periplasmic extraction buffer in blood meals containing all the *E.coli* used to make the periplasmic extract (100% (v/v) inoculum) (4A and 4B) and then the effect of inoculum volume (blood to periplasmic extract at a constant ratio of 4:1) (4C and 4D) was determined. All values and error bars represent the mean and standard deviation of three independent experiments.

FIG. 5 shows the estimation of cross-contamination between clones. A chess-board structured array of pCANTAB-6 (no scFv insert) and anti-FITC-E2 (high scFv-producing clone) were presented to a cage of *Anopheles gambiae*. Phage-packaged phagemids were successfully recovered from 21/22 mosquitoes chosen at random 24-hour post-feeding. The phagemids were then reinfected into *Escherichia coli* HB2151 and eight randomly chosen colonies cultured under scFv-inducing conditions. Antibody fragment expression in these cultures was detected by dot-blotting. The anti-FITC-E2 clone, which produces abundant scFv, is readily distinguished from the control (pCANTAB-6) by dot-blot hybridization.

DETAILED DESCRIPTION OF THE INVENTION

It is proposed that if clones within a library of nucleic acid sequences exert in vivo effects which can be detected in single insects, it should be possible to identify such clones by a strategy which is herein termed single insect feeding, testing and recovery (SIFTER). The principle of the strategy is that the nucleic acid sequences (genotypes) of clones from a library are coupled to their observable effects (phenotypes) in individual animals randomly feeding from an array of single clones. Phenotypically-desirable clones from a library representing a pool of genotypes may be isolated by a) allowing individual insects to feed on clones from the library, presented as an array, and b) recovering clones from individual test insects showing the desired phenotypic impact. It is further proposed that the single-insect feeding, testing and recovery strategy is applicable to any biological activity, library and insect for which the following criteria can be fulfilled: a) an individual must sample the presented arrays sufficiently and each individual should usually sample only one clone; b) the clone must be recoverable from the individual; c) the desired biological activity should be readily and rapidly identifiable; and d) the background level of false positives for the sought biological activity must be sufficiently low to meaningfully reduce the burden of further screening positive clones. The principle is equally applicable to arthropods other than insects and to screening panels of biomolecules and/or naturally occurring microbes rather than recombinant nucleic acid libraries.

Mosquitoes were chosen to develop a model for single-insect feeding, testing and recovery screening because they are major vectors of many important human pathogens, notably malaria, and because new tools are clearly needed to adequately control the transmission of malaria in endemic areas, particularly in sub-Saharan Africa. Immunization of laboratory animals with crude preparations from mosquito tissues can induce immune responses which reduce the longevity (Noden et al., 1995, Alger & Cabrera, 1972, Ramasamy et al., 1992, Hatfield, 1988, Almeida & Billingsley, 1998), reproductive fitness (Ramasamy et al., 1992, Ramasamy et al., 1988, Sutherland & Ewen, 1974, Noden et al., 1995) and pathogen transmission capacity (Ramasamy & Ramasamy, 1990, Ramasamy et al., 1990, Ramasamy et al., 1997, Srikrishnaraj et al., 1995, Lal et al., 1994) of mosquitoes when the mosquitoes subsequently feed upon the immunized animals. In the working example disclosed herein, insect mortality was screened as the biological activity because it is easy to observe and because a biomolecule capable of killing *Anopheles gambiae* mosquitoes could provide an anti-vector vaccine to combat malaria transmission. Malaria in Africa is largely transmitted by highly anthropophilic, long-lived mosquito species whose vectorial capacity is extremely sensitive to alterations in mortality rates (Billingsley, 1994).

Figure 1:
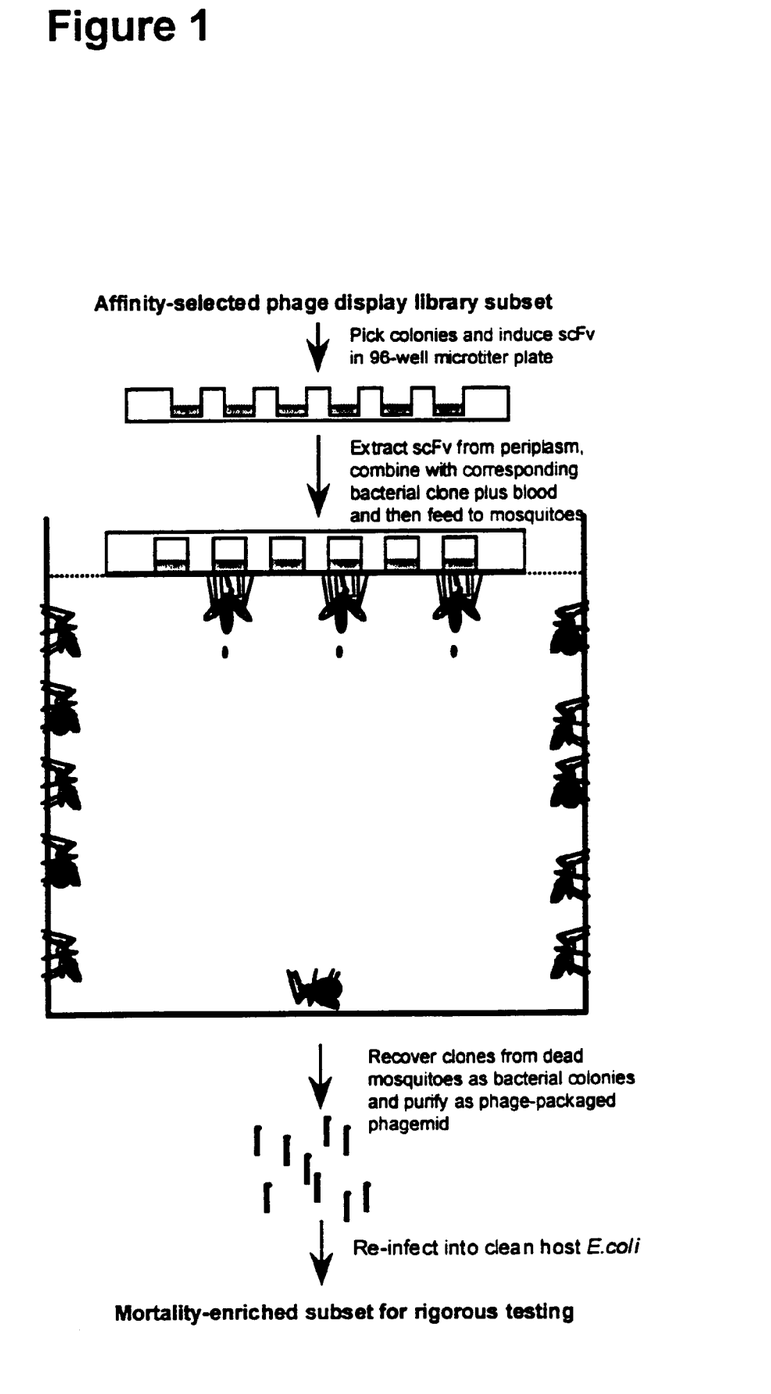
FIG. 1 shows an overview of the single-insect feeding, testing and recovery (SIFTER) screening system in which an embodiment is shown for identifying scFv-producing phagemid clones which kill *Anopheles gambiae* mosquitoes.

The development of a model screening system using the SIFTER strategy of the present invention is described herein. In the working example disclosed, the invention is used to screen arrays of single clones from a phage-display library of human antibody constructs for clones capable of killing the malaria vector mosquito, *A. gambiae*. Arrays of antibody fragments were fed to cages of mosquitoes as a combination of expressed single chain variable region fragments (scFv) and bacteria containing the phagemids which encode them (FIG. 1). The screening system of the present invention greatly reduced the burden of laborious single-clone tests, although no mosquito-killing clones were identified in the array of clones presented to the mosquitoes. The performance of the model screening system, with respect to the four proposed criteria, is described and other model screening systems based upon the SIFTER strategy are embodied.

The present invention is directed towards a SIFTER screening strategy to identify and isolate biologically active molecules directed towards arthropods.

The present invention is directed towards a method of screening for a biologically active molecule directed towards a species of arthropod, comprising the steps of: (a) feeding an array of biomolecules to a population of a species of arthropods, wherein individual arthropods preferably feed on a single biomolecule; (b) testing the arthropods for a desired phenotype, wherein the desired phenotype is indicative of one or more biomolecules possessing biological activity towards the species of arthropod. The above-described method also comprises the step of: (c) recovering the biomolecule(s) resulting in the desired phenotype from the arthropods displaying the desired phenotype. Preferably, the arthropod is a mosquito, and more preferably, the mosquito is *Anopheles gambiae*.

The present invention is still further directed towards a method of screening for a biologically active molecule directed towards the malaria vector mosquito, *Anopheles gambiae*, comprising the steps of: (a) feeding an array of biomolecules to a population of *Anopheles gambiae*, wherein individual *Anopheles gambiae* preferably feed on a single biomolecule; (b) testing the *Anopheles gambiae* for a desired phenotype, wherein the desired phenotype is indicative of one or more biomolecules possessing biological activity towards the *Anopheles gambiae*; and (c) recovering the biomolecule(s) resulting in the desired phenotype from the midgut of the *Anopheles gambiae* displaying the desired phenotype.

The above-described methods may further comprise the steps of: performing iterative cycles of steps (a), (b) and (c) until the biomolecule(s) are purified, and additionally, may further comprise the step of: enriching the array of biomolecules for midgut-specific biomolecules prior to the feeding.

Generally, the array of biomolecules may be an expression library, the products from an expression library, any library of nucleic acid fragments, naturally-occuring microbes, viruses or genetically modified forms thereof. Typically the expression library is a phagemid library, a phage-display library, a eukaryotic nucleic acid vector-based expression library, a prokaryotic nucleic acid vector-based expression library, or any other library of nucleic acid fragments with the potential to exhibit a phenotype in an arthropod. Representative biomolecules resulting in the desired phenotype are a toxin, a monoclonal antibody, a polyclonal antibody, a single-chain antibody, a naturally occurring microbe, pathogen-refractory genes, genes encoding receptors for pathogen invasion, or any other gene with the potential to alter arthropod longevity or vector competence.

It will be apparent to one skilled in the art that various substitutions and modifications may be made to the invention disclosed herein without departing from the scope and spirit of the invention.

As used herein, the term "array" refers to any set of spatially separated sub-units, referred to as "elements", each of which contains a different biomolecule or mixture of biomolecules, and presented to insects as alternative possible meal choices.

As used herein, the terms "biomolecule" or "biologically active molecule" refer to any nucleic acid sequence or its transcription product or its translation product or its final expression product or to the biological activity, genotype or phenotype it confers.

As used herein, the term "element" refers to the spatially separated sub-units of an array, each of which contain different individual clones or mixtures of clones.

As used herein, the term "vector" refers to an intermediate host for a pathogen, except where it is specified as a "nucleic acid vector", in which case it refers to a nucleic acid construct for propagation and manipulation of nucleic acid sequences.

The following examples are given for the purpose of illustrating various embodiments of the invention and are not meant to limit the present invention in any fashion:

The following abbreviations may be used herein: Anti-FITC-E2, Monoclonal scFv against fluorescein conjugates; ECL™, Enhanced chemiluminescence; IPTG, Isopropyl-β-D-thiogalactopyranoside; MAG, Minimal medium plus ampicillin and glucose; PBS, Phosphate-buffered saline; scFv, Single chain variable region antibody fragment; SIFTER, single-insect feeding, testing and recovery; SEM, Standard error of the mean; tu, transforming units; 2TY, Tryptone-yeast extract medium; 2TYAI, 2TY plus ampicillin and IPTG; 2TYAG, 2TY plus ampicillin and glucose.

EXAMPLE 1

Mosquito Rearing and Handling

An *A. gambiae* G3 colony was maintained in an insectary at 27° C., 80% relative humidity. Larvae were fed finely ground fish food and adults were provided with 10% (v/v) KARO™ cane syrup and water. Pupae were allowed to emerge in bleach-cleaned 1 gallon plastic cages lined with clean disposable paper towels and the emerging adults were experimentally fed through PARAFILM™ membranes from single-chamber membrane feeders or microtiter plates at 3–6 days post emergence.

EXAMPLE 2

Antibody Fragment Library and Panning

The library of $1.4 \times 10^{10}$ different human single-chain variable region fragment (scFv) constructs in the phage-display nucleic acid vector pCANTAB-6 (McCafferty et al., 1994) and routine methods for scFv isolation (Vaughan et al., 1996) have been described. The high diversity of this library has allowed the isolation of antibody fragments specific for a variety of antigens, to which the original donors were naive (never exposed). These antigens even include haptens and even self-antigens (Vaughan et al., 1996). Antigen-specific clones selected from this specific phage display library typically yield 2–1000 ng of scFv per ml of culture, with expression level being highly dependent on the sequence of the particular clone (McCafferty & Johnson, 1996, Vaughan et al., 1998, Vaughan et al., 1996).

Initially, the phage display library comprising human scFv constructs was panned on mixed antigens from the midgut of *A. gambiae* by three rounds of selection as follows. Phage particles, tagged with their encoded scFv as fusion proteins with the phage gene 3 protein, were recovered from the phagemid library in *E. coli* host cells of the suppressor strain TG1 (K12, Δ(lac-pro) supE thi hsdΔ5 [F' traΔ36 proA$^+$B$^+$ lacI$^q$ lacZΔM15]) (Vaughan et al., 1996). Mixtures of midgut antigens were prepared by grinding 60 freshly dissected midguts in 1 ml of ice-cold phosphate buffered saline (PBS) (10 mM Na-phosphate, 150 mM NaCl (pH 7.4)). Soluble antigens were removed by resuspending and centrifuging three times at 8000 g for 10 min in fresh 1 ml aliquots of cold PBS. The remaining pellet of particulate insoluble antigens was then used to pan the phage-displayed scFv. Both the scFv-tagged phage particles ($10^{12}$ tu) and insoluble midgut antigens were each blocked in 0.5 ml of 100 μg ml$^{-1}$ bovine serum albumin in PBS at 37° C. for 1 hr and then mixed. The particulates were allowed to stand at room temperature for 1 hr and were then washed by resuspending in cold 0.1% (w/v) Tween 20 in PBS followed by washes in PBS (3×1 ml each) and then centrifuged at 8000 g for 15 min. Remaining phage were then reinfected into log-phase *E. coli* TG1, which were titered and propogated on 2TY containing 100 μg ml$^{-1}$ ampicillin and 2% D-glucose (2TYAG) (McCafferty & Johnson, 1996). Phage particles were recovered from these cells (McCafferty & Johnson, 1996) and this panning process to enhance for midgut-specific scFv constructs repeated twice.

EXAMPLE 3

Soluble Antibody Fragment Expression

Phage-displaying scFv clones selected from the panning process were transferred via infective phage to the non-suppressor *E. coli* strain, HB2151 (K12, Δ(lac-pro) ara NaI' thi [F' proA$^+$B$^+$ lacI$^q$ lacZΔM15]) for the production of soluble scFv without fusion protein. The phage-containing bacteria were then propagated on minimal agar medium containing M9 salts (McCafferty & Johnson, 1996), 100 μg ml$^{-1}$ ampicillin and 2% (w/v) D-glucose (MAG). Maintenance on MAG allows the use of this same selective medium to recover bacteria from the mosquito midgut, such that phage-packaged phagemid can then be recovered from the bacterial colonies, since MAG is selective for phagemid-bearing male *E. coli* (bearing an F' pilus).

Cultures (400 μl) of picked clones in 24-well tissue culture clusters were grown overnight to stationary phase in 2TYAG at 30° C. in a humidity chamber, reactivated by adding an additional 1 ml of fresh 2TYAG and then incubated for 1 hr at 30° C. Soluble scFv production was induced by centrifuging at 2000 g for 15 min and subsequently resuspending the cells in 1 ml 2TY containing 100 μg ml$^{-1}$ ampicillin and 1 mM IPTG (2TYAI) and incubating at 30° C. for 4 hr. The cultures were centrifuged at 2000 g for 15 min and resuspended in 200 μl of 2TYAI for transfer to 96-well plates in which the cultures were recentrifuged. Under the finalized SIFTER conditions (inoculum of 2.5% of the induced *E. coli*), 5 μl of this concentrated suspension of bacteria were put aside in a replica plate to serve as the bacterial inoculum in the bloodmeal. Soluble scfv in the bacterial periplasm was extracted by resuspending in 20 μl of hypertonic extraction buffer (20% (w/v) sucrose, 1 mM EDTA, 50 mM Tris-HCl (pH 8.0)) and allowing the mixture to stand on ice for 15 min. Bacterial cells were removed by centrifugation.

EXAMPLE 4

Detection of Antibody Fragments

Antibody fragments in periplasmic extracts and in tissues from mosquitoes which had fed on the antibody fragments were detected by adsorbing extracted scFvs to polyvinylidene fluoride membranes (Amersham-Pharmacia) using a vacuum manifold dot blot apparatus (Bio-Rad) and visualized (McCafferty & Johnson, 1996). Briefly, scFvs were detected by probing with the 9E 10 monoclonal mouse antibody (Sigma), which is specific for the c-myc epitope expressed contiguously with the scFv in the pCANTAB-6 nucleic acid vector (McCafferty & Johnson, 1996). Reactive dots were then visualized with horseradish peroxidase-conjugated sheep anti-mouse IgG (Sigma) and recorded with enhanced chemiluminescence (ECL™) reagents and ECL™ film (Amersham-Pharmacia). Mosquitoes fed scFv with blood from a microtiter plate were harvested after 12 hr, dissected and the midguts and carcass (all other tissues) were individually and separately washed by suspending and centrifuging at 2000 g for 15 min in 1 mM phenyl-methyl-sulphonyl fluoride in PBS (3×50 μl). Antibody fragments were then extracted by heating at 95° C. in 50 μl Laemmli buffer. Such extracts were clarified by diluting with 200 μl of PBS and centrifuging at 8000 g for 10 min before dot-blotting the supernatant. Periplasmic extracts were also diluted 5-fold in PBS and centrifuged before adsorbing to the membrane.

EXAMPLE 5

Screening by Single Insect Feeding, Testing and Recovery (SIFTER)

An overview of SIFTER screening is depicted in FIG. 1. Pupae were placed in the cages at the required density (250 to 300 females per cage) so that no handling was necessary post-emergence. In initial experiments in which single clones or arrays of clones were fed to mosquitoes and subsequently recovered, the bacterial cells from which scFv had been extracted were not removed from the periplasmic extract before the addition of human blood (40% hematocrit in heat-inactivated serum) prior to feeding. In the finalized SIFTER method, the bacterial pellet was removed by centrifugation and the periplasmic extracts of each clone added to their corresponding inoculum in the replica plate prepared before extraction. Blood (75 μl) was added to each well and mixed thoroughly (but without foaming) by pipette action. When feeding from microtiter plates, the Parafilm™ membrane was stretched across the surface of the prewarmed plate (37° C. for 15 min), inverted and lightly shaken once to place the bloodmeal in contact with the membrane surface. The inverted plate was then placed in contact with the netting at the top of the cage and was not moved until termination of the feed 60 min later. At the start of the feed, a 200 ml reservoir of warm (50° C.) water was placed on top of the plate and the water carefully removed and replaced with a small beaker containing warm water at 15 min intervals. It is important to avoid disturbing the contact between the membrane and the plate to prevent leakage, and hence, intermixing of bloodmeals from adjacent wells. It is therefore critical that the array be prewarmed to prevent expansion of air within the well after the membrane is applied and that neither the cage, the array, or the warm water reservoir are disrupted after assembly.

Clones were recovered from individual dead mosquitoes by surface sterilizing the mosquito for 5–10 min in 70% ethanol, dissecting out the midgut and suspending their bloodmeals in 500 μl of PBS before streaking on MAG. Recovered colonies, including both phagemid-containing *E. coli* and midgut microflora contaminants, were pooled by suspending all the colonies from the plate in a single 10 ml aliquot of 2TYAG and purified as infective phage particles (McCafferty & Johnson, 1996). The phage-particles were sterilized by filtration and reinfected into fresh *E. coli* HB2151 cells to yield phagemid free of bacterial and plasmid contaminants from the microflora of the mosquito midgut.

EXAMPLE 6

Single Clone Feeding

All feedings of single scFv preparation to cages of 30–60 mosquitoes were carried out using standard water-jacketed feeders (Ponnudurai et al., 1989) and Parafilm™ membranes. Cultures of pCANTAB-6, each in a 10 ml volume, were grown and induced under identical conditions and fed individually to cages of 60–100 females to test SIFTER conditions. In order to test different, these larger cultures provided enough bacteria to test different inoculum sizes (i.e., doses of bacteria) which were added to mixtures of periplasmic extract and blood. These mixtures of blood and periplasmic extract were in a 4:1 ratio unless stated otherwise. Clones identified and enriched under finalized SIFTER conditions were rigorously tested for mosquito-killing activity, relative to pCANTAB-6 controls, using the same protocol.

EXAMPLE 7

Optimization and Characterization of SIFTER Screening

The SIFTER protocol was optimized for mosquito-killing scFv screening, by varying blood-periplasmic extract ratio and bacterial inclusion levels. Mosquito rearing and cage design were then tailored to allow minimal handling and mortality. Such adaptations included the regular provision of fresh, well soaked water and sugar pads and the taping of paper of towels to the sides of the cage so that they were flush with the cage, leaving no gaps for insects to become trapped. The efficiency of array sampling, clone recovery and the extent to which mosquitoes fed on only one well was then assessed. A clone specific for fluorescein conjugates (anti-FITC-E2), isolated previously from this library and known to produce abundant scFv (Vaughan et al., 1996), and the pCANTAB-6 control nucleic acid vector were chosen to assess whether phagemids recovered from individual mosquitoes indeed encode monoclonal antibodies, since these two clones are readily distinguished in *E. coli* HB2151. These two clones were arranged in a chessboard-structured array and presented to a cage of mosquitoes for random sampling.

In order to assess the efficiency of the SIFTER method with respect to its ability to reduce the number of individual clones which need to be rigorously tested, 8 arrays of 96 clones each (768 total clones) picked at random from the midgut-selected scFv panel were fed to eight cages of mosquitoes. Feeding rates were assessed in the first four arrays by removing and counting unfed mosquitoes immediately after removal of the microtiter plate feeding array and subsequently counting the total number of dead and surviving fed mosquitoes over the course of the experiment.

EXAMPLE 8

Screening by Single Insect Feeding, Testing and Recovery

Figure 2:
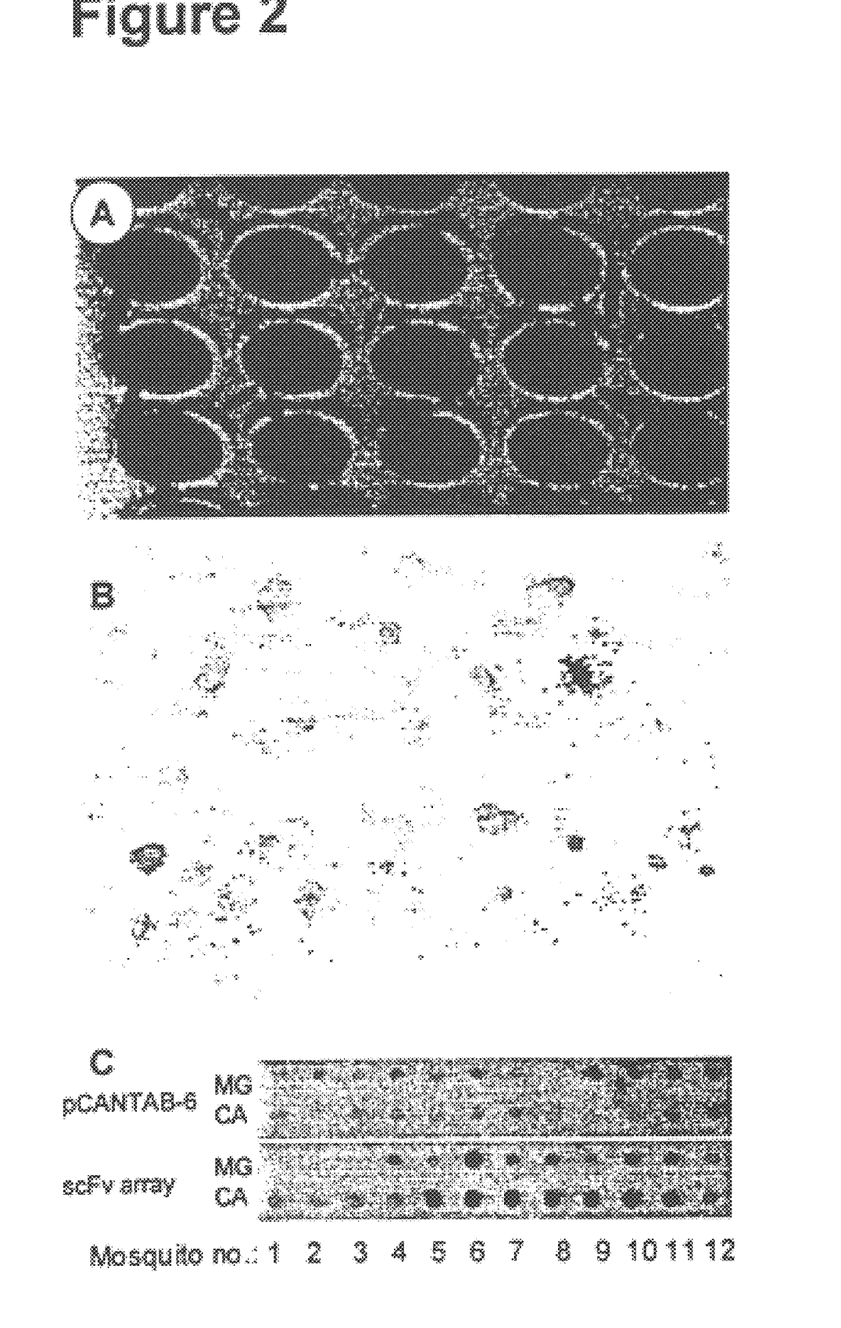
FIG. 2 shows *Anopheles gambiae* feeding mosquitoes arrays of scFv from microtiter plates.

When blood was presented to cages of mosquitoes in 96-well microtiter plates, 60 to 90% of female mosquitoes engorged and individual mosquitoes were observed to feed from only one of the presented array of wells (FIG. 2A). The observed pattern of pre-diuretic fluid collected on the bottom of cages with 250–300 female *A. gambiae* demonstrates sampling throughout the presented microtiter plate (FIG. 2B). When an array of 96 monoclonal scFv from a human scFv library phage-display selected on *A. gambiae* midguts was presented in combination with blood to the cage of mosquitoes, scFv was detected in the midguts and other tissues of individual mosquitoes (FIG. 2C).

Figure 3:
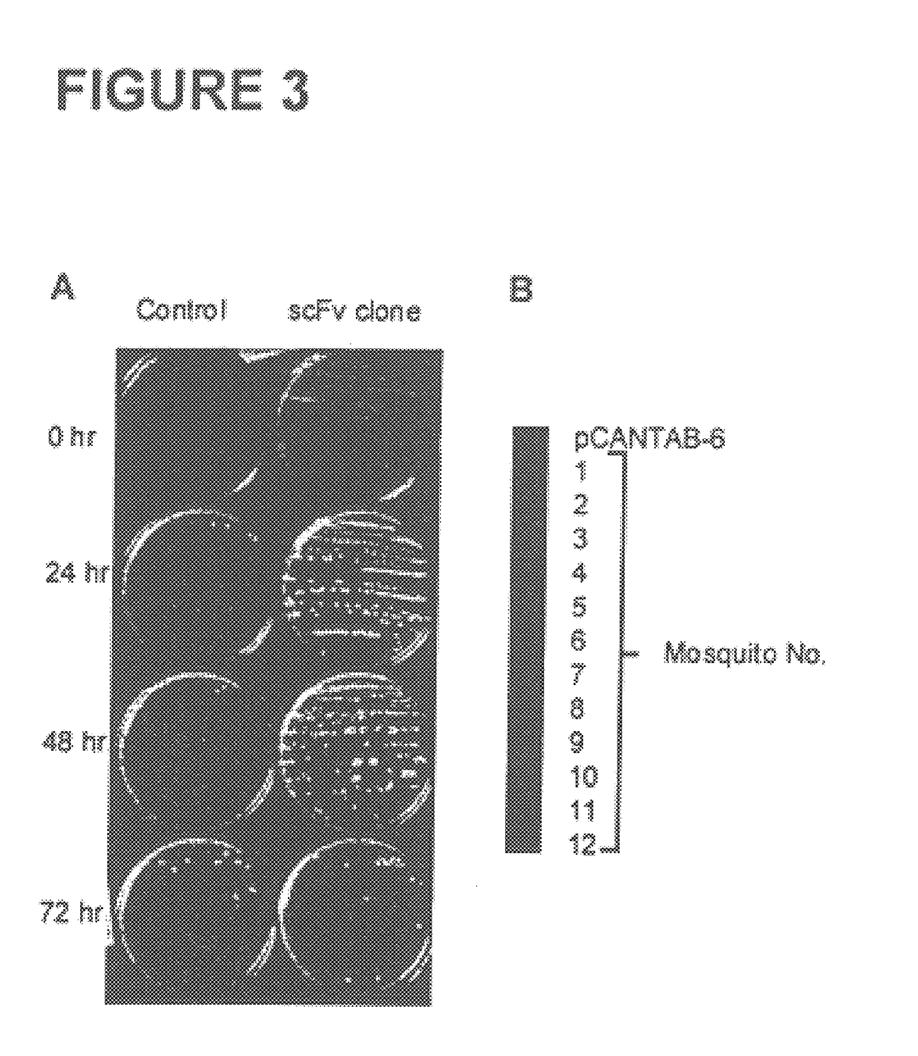
FIG. 3 shows the recovery of phagemid clones from mosquitoes fed arrays of bloodmeals containing a mixture of scFv-containing periplasmic extracts and the phagemid-containing bacteria from which they were derived.

Using the anti-FITC-E2 as an example of a clone that produces abundant scFv (Vaughan et al., 1996), phagemid-containing bacteria from which scFv had been extracted were easily recovered from the mosquito up to 48 hr post feeding by streaking out the midgut contents on selective agar (FIG. 3A). Contaminant colonies from the midgut microflora were also often observed, and although some of them could be differentiated on the basis of colony morphology, many could not. However, desirable clones were readily purified by recovering as phage-packaged phagemids. Phage were successfully rescued from the resuspended pools of all colonies recovered on agar plates and re-infected into fresh host cells to remove contaminating bacteria or plasmids from the midgut microflora. Phage-packaged clones were successfully recovered from mosquitoes (12/12) which died within 12 hr of feeding. Furthermore, all 12 clones expressed detectable levels of scFv (FIG. 3B).

Figure 4:
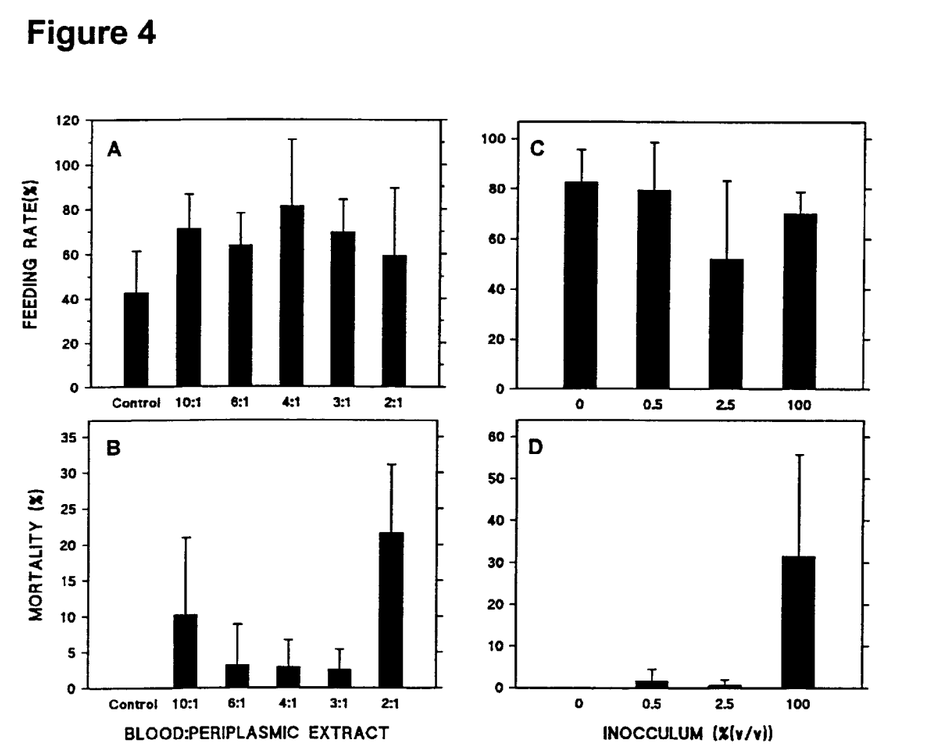

None of the 12 scFv-producing clones initially isolated from dead mosquitoes (FIG. 3B) were found to kill when periplasmic extracts from bacteria carrying each clone was subsequently fed individually to cages of 30–60 mosquitoes using conventional membrane feeders. In the initial SIFTER experiments (FIGS. 2 and 3), mixtures of blood and periplasmic extracts presented to mosquitoes were inoculated with the entire pellet of extracted bacteria. High mortality rates (up to 64% after 48 hr) were observed, but were not caused by any mosquitocidal scFv since identical mortality rates were observed when pCANTAB-6 (the phagemid nucleic acid vector lacking an scFv insert) was fed to the mosquitoes (FIG. 4D). The bloodmeals of mosquitoes fed blood-periplasm mixtures containing such high densities of *E. coli* darkened rapidly, suggesting that excessive proteolytic fermentation of the bloodmeal was the cause of this high mortality. Subsequent tests showed that high densities of *E. coli* were indeed responsible (FIG. 4D).

EXAMPLE 9

Optimization of SIFTER to Screen for Mosquito-killing Clones

In order to reduce the number of false positives yielded by the primary screen, the ratio of blood to periplasmic extract was optimized using the pCANTAB-6 nucleic acid vector alone as a negative control (FIGS. 4A and 4B). Interestingly, mosquitoes appear to prefer blood with suspensions of nucleic acid vector-containing *E. coli* in the periplasmic extraction buffer to blood alone; feeding rates in all the treatment groups (n=15) in FIG. 4A averaged (±SEM) 69.1±5.2%, whereas those in the blood plus extraction buffer control (n=3) were 42.7±10.7% (P=0.052). Reduction of the number of bacteria used to inoculate the bloodmeal greatly reduced background mortality without significantly reducing feeding rates (FIGS. 4C and 4D) or the ability to recover clones from the midgut. Based on these observations, subsequent SIFTER experiments were conducted with an inoculum of 2.5% (v/v) of induced bacteria and a 4:1 ratio of blood to periplasmic extract.

EXAMPLE 10

Characterization of Optimized SIFTER Screening Efficiency

Figure 5:
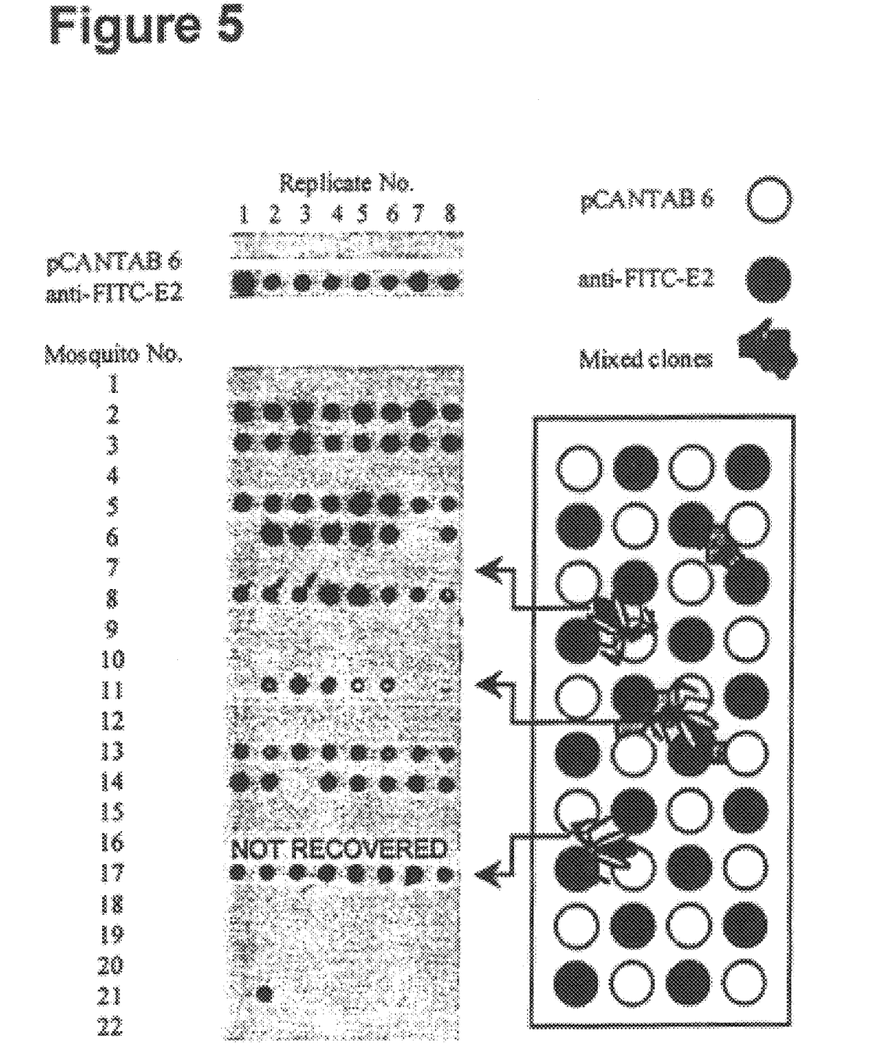

After feeding the chessboard array to test the monoclonality of recovered phagemids, phage-purified clones were successfully recovered from 21/22 (95%) dissected mosquitoes (FIG. 5). Eight colonies were picked at random from phage-recovered clones, cultured under scFv-inducing conditions and tested for scFv production by dot blotting. Six of the phagemid preparations which were successfully recovered from mosquitoes appeared to be monoclonal anti-FITC-E2 (FIG. 5). An additional 11 clones selected appeared to be monoclonal pCANTAB-6, because none of the picked colonies produced scFv (FIG. 5). Thus, 17/21 (81%) of recovered clones appeared to be monoclonal. The remaining scFv-expresssing phagemid preparations recovered from mosquitoes yielded predominantly a single clone with light contamination of the other (1/8 or 2/8) (FIG. 5). Presumably, such mixed phagemid recoveries resulted from mosquitoes which either fed on two separate wells or which fed on mixed clones at occasional portions of the plate where well-leakage and hence, cross-contamination, occurred between wells.

Based on these estimates of cross-contamination, it is calculated that the chance of picking a contaminant rather than a dominant clone (C) from a single colony recovered via phage rescue from a single mosquito was only 0.036 (C=(1/8×2/21)+(2/8×2/21)). Allowing for the possibility of not recovering a clone or of recovering the wrong clone, clone recovery was estimated to be 92% efficient (Recovery efficiency (E)=Recovery rate (R)×Recovery accuracy (A)=(1−C)×R=(1−0.036)×0.95=0.92).

In order to assess the efficiency of the SIFTER method in terms of optimization to reduce the number of clones which need to be individually and rigorously tested, eight arrays of 96 clones (768 clones), picked at random from the midgut-panned scFv library, were fed to 8 cages of mosquitoes. The numbers of blood-fed mosquitoes were counted in the first four experiments and an average of 211 (range 179–244) fed from each array. Assuming that individual mosquitoes sample single wells chosen from a 96-clone array randomly, the chance of a given clone remaining unsampled at the end of the feed is $(95/96)^n$, where n is the number of mosquitoes which engorge from the array. Thus, N, the probable number of clones from an array which are sampled during a SIFTER experiment, can be calculated as $96 \times (1−(95/96)^n)$. This predicts an average (±SEM) number, N, of 85.2±1.57 clones sampled in each array, or 682 of the 768 screened clones (88%).

A total of 5 and 9 mosquitoes died on the first and second days post-feeding, respectively. Clones were successfully recovered from all 14 mosquitoes that died and the isolated clones were subsequently fed individually to cages of 40–60 mosquitoes. Estimated losses (L) due to unsampled, unrecovered and cross-contaminant clones total 18% of induced and presented clones (L=1−(N/96×E)=1−(0.88×0.92)=0.18). Thus, the 14 clones recovered from dead mosquitoes are actually equivalent to those which would be yielded by screening 627 perfectly sampled and recovered clones (Effective number of clones screened (S)=Estimated number of sampled clones (N)×Recovery efficiency (E)=682×0.92=627).

Thus the equivalent of 627 clones were screened in the experiments described herein, yielding 14 candidate clones which required more rigorous and laborious individual testing for killing activity. The reduction in the burden of individual testing is clear when one considers that conventional methods would require 627 clones to be examined individually to achieve an equivalent screen. This represents a 125- or 48-fold reduction in the number of clones which need to be individually tested, depending on whether 24 or 48 hr are allowed for the desired phenotype to be observed (in this case, for death to occur).

None of the 14 clones recovered in this trial of the SIFTER system were found to kill *A. gambiae* mosquitoes. In hindsight, it is not surprising that no mosquitocidal clones were isolated because the scFv library subset described here was not significantly enriched for midgut-specific clones by the phage display selection on mosquito midgut described herein. Although the selection output titers were high (approximately $1 \times 10^6$ tu), the titers did not increase with progressive rounds of panning. It has since been determined that selections with pCANTAB-6, the nucleic acid vector without a n insert, yield identical outputs, indicating that efficient selection was prevented by adsorption of the phage capsid itself to the mosquito midgut preparations. This phenomenon has also been reported as a possible explanation for the lack of enrichment of phage-displayed *Bacillus thuringiensis* Cry1Ac when panned on gut preparations from *Manduca sexta* larvae (Kasman et al., 1998).

EXAMPLE 11

Performance of the Model Screening System

The SIFTER-based screening model described herein made it possible to screen hundreds of recombinant antibody fragments for their ability to kill *A. gambiae* mosquitoes within one or two days of a bloodmeal. This represents an increase of at least an order of magnitude over the current rate at which libraries can be screened in insects for in vivo biological activities. The value of the SIFTER strategy is clear when compared with conventional membrane-feeding techniques in which single preparations are fed to cages of 20 or more mosquitoes and their impact on survival monitored over periods of a week or more (Noden et al., 1995, Willadsen & Billingsley, 1996, Almeida & Billingsley, 1998). Although no mosquitocidal scFv were identified in this selection from the library, panning techniques which facilitate selection of scFv panels with specificities for mosquito midgut antigens are currently being developed (Marzari et al., 1997, Kasman et al., 1998). Although further pursuit of mosquitocidal scFv awaits such developments, a screening system based on the SIFTER strategy, which is considerably faster than conventional methods, has been successfully demonstrated herein. The performance of this model system, with respect to the four prerequisites for SIFTER screening, are discussed below in the context of additional embodiments.

EXAMPLE 12

Criterion 1

Representative and Monoclonal Sampling of the Arrays

Firstly, groups of insects must sample the presented arrays sufficiently, but individuals should preferably sample only one element (i.e., clone or small pool of clones) of the array. This is largely a function of feeding behavior and the rearing and handling systems available. In the SIFTER screening model embodied herein, individual *A. gambiae* females feed predominantly from single wells and cages of mosquitoes sample the majority of the presented arrays. It is interesting to note that *A. gambiae* actually prefers mixtures of bacteria and periplasmic extracts to blood alone. This may result from the role that bacterial fermentation products play in the behavior of this anthropophilic mosquito species (Knols, 1996). It is also noteworthy that the delivery of scFv to tissues other than the midgut (FIG. 2C) is consistent with previous demonstrations of ingested antibodies entering the mosquito hemolymph (Jacobs-Lorena & Lemos, 1995, Willadsen & Billingsley, 1996, do Rosario et al., 1989, Vaughan & Azad, 1988, Vaughan et al., 1988, Lackie & Gavin, 1989).

Although *A. gambiae* has suitable feeding habits and is relatively easy to rear and handle, other arthropod systems will require adaptation. Further applications with mosquitoes (Galun et al., 1985) and other hematophagous insects (Friend & Smith, 1982) could use phagostimulants, such as nucleotides, as an alternative to whole blood. In principle, elements in the presented arrays need not necessarily consist of single clones; each array element may consist of small pools of clones and, where practically compatible, SIFTER-like strategies may be combined with iterative in vitro expression cloning strategies (King et al., 1997). Iterative in vitro expression cloning strategies are those in which libraries are initially screened for biological activity as a small number of pools containing large numbers of clones, following which, pools found to be active are subdivided and the process re-iterated until single clones with biological activity are identified (King et al., 1997). Expression libraries in which the expressed proteins are secreted into the periplasm of their *E. coli* hosts may be particularly amenable to such screening in many arthropods, especially sugar feeders, because the expressed molecules can be extracted with sucrose buffers. Alternatively, DNA sequences could be delivered in viral (Matsubara et al., 1996, Olson et al., 1996) or bacterial (Durvasula et al., 1997) nucleic acid vectors and subsequently act in situ, rather than requiring inclusion of the expressed gene product in the bloodmeal.

EXAMPLE 13

Criterion 2

Recovery of Consumed Clones

Secondly, the nucleic acid sequence(s) or genotype(s) of the consumed element must be subsequently recoverable from individual insects. This is necessary to allow screening without the necessity to compartmentalize large pools of test insects into experimental units or to know which individual arthropods fed upon which clone. Although it was relatively easy to recover *E. coli* and the existing pCANTAB-6 nucleic acid vector from *A. gambiae*, other common recombinant hosts may not be viable in the midguts of other arthropods. Phage particles represent an alternative form in which nucleic acid sequences are delivered and recovered. Bacterial delivery systems for other invertebrates may necessitate the development of shuttle nucleic acid vectors and alternative expression hosts, as has been achieved in *Rhodnius prolixus* (Durvasula et al., 1997). Recombinant insect viruses could be recovered as virus particles or isolated nucleic acids (Matsubara et al., 1996, Olson et al., 1996). Perhaps the simplest recovery system which can be envisaged is one in which panels of environmentally-occurring microbes are cultured and screened by SIFTER methods for those which, like *B. thuringiensis*, can kill insects. Such expression and/or delivery systems could be used throughout panning and cloning. Alternatively, selections panned in phage-display systems could be subcloned into such alternative systems where they are more appropriate to screen for biological activity.

EXAMPLE 14

Criterion 3

Phenotype Identification

Thirdly, the biological activity sought must be rapidly and readily identifiable or its detection may limit the speed with which libraries can be screened. It remains to be seen whether mosquitocidal scfv can be selected from this library and expressed in sufficient abundance by this phagemid system to kill mosquitoes under the conditions of the model described. Nevertheless, the phenotype itself is unmistakable and ideally suited to SIFTER screening because only those mosquitoes which die need to be processed. Limitations in the current ability to select and express potentially mosquitocidal antibodies do not negate the suitability of this useful phenotype (i.e., death) for SIFTER-based screening applications.

The detection of more subtle phenotypes, such as the blocking of infectivity of a pathogen to the arthropod, are also embodied in the instant invention. Traditional methods for detecting infections of viruses and parasites in individual arthropods, such as microscopy, PCR or ELISA, will suffice, but are typically laborious when screening large libraries. However, the green fluorescent protein of *Aequorea Victoria* has recently been expressed in the human malaria parasite, *Plasmodium falciparum* (VanWye & Haldar, 1997) and developed as a marker of viral infections, notably in mosquitoes (Higgs et al., 1996). Furthermore, the progress of infection by such labeled viruses is readily visualized in plants at the macroscopic level (Oparka et al., 1997) and molecules which block the transmission of viral and protozoan pathogens to their arthropod vectors are similarly screened.

EXAMPLE 15

Criterion 4

Minimizing False Positives

Fourthly, the background level of false positives for the sought biological activity must be sufficiently low to allow useful reductions in the number of rigorous tests which must be executed. This is because the amount of time saved is an inverse function of such background levels. In the example taught herein, the SIFTER system has been tailored by refining rearing, handling and screening protocols so that the background mortality is low enough to reduce the burden of single-clone testing by up to 125-fold. For transmission-blocking screens, it is essential that the infection process be very close to 100% efficient and robust to the addition of such crude bacterial extracts. For example, it may be difficult to develop SIFTER-based methods for the identification of molecules which block the infection of mosquitoes by cultured *P. falciparum* because it is difficult to routinely infect >90% of fed mosquitoes Noden et al., 1994).

EXAMPLE 16

Future Potential of SIFTER for the Isolation of scFv Which Kill Mosquitoes

Although their mechanisms of action are not yet clear, the ability of antibodies to kill arthropods, including insects such as blowflies, stable flies, sandflies and tsetse, is well established (Jacobs-Lorena & Lemos, 1995, Willadsen & Billingsley, 1996, Almeida & Billingsley, 1998). More specifically, there is also reasonable (Noden et al., 1995, Alger & Cabrera, 1972, Ramasamy et al., 1992, Hatfield, 1988, Almeida & Billingsley, 1998), if not conclusive (Jacobs-Lorena & Lemos, 1995), evidence that polyclonal antibodies can be toxic to mosquitoes, and it remains to be proven that monoclonal antibodies can do the same (Jacobs-Lorena & Lemos, 1995, Willadsen & Billingsley, 1996). Although no monoclonal antibody with insecticidal activity has been isolated to date, this is quite possibly because attempts to do so have been impeded by technical obstacles (Jacobs-Lorena & Lemos, 1995, Willadsen & Billingsley, 1996, Almeida & Billingsley, 1998). With the notable exception of the cattle tick, *Boophilus microplus*, methodological limitations have prevented the identification of antigens suitable for vaccine development (Jacobs-Lorena & Lemos, 1995, Willadsen & Billingsley, 1996). Conventional methods for producing and testing either polyclonal or monoclonal antibodies are clearly limiting investigations which might lead to anti-vector vaccines (Jacobs-Lorena & Lemos, 1995, Willadsen & Billingsley, 1996, Almeida & Billingsley, 1998).

The present inventors, as well as other groups (Marzari et al., 1997, Kasman et al., 1998), are now developing techniques suitable for selecting insect midgut antigen mixtures. The anticipated availability of more promising scFv subsets and suitable baculovirus selection and expression systems (Granziero et al., 1997, Ernst et al., 1998) may facilitate the isolation of additionally useful antibody clones for use in SIFTER-based screening strategies. However, this is just an example of one library and technology to which the SIFTER strategy can be applied. Pre-selection and enrichment for selected types of clones is not necessarily a prerequisite for screening by SIFTER-based methods and may not be required for other libraries and technologies.

EXAMPLE 17

Other Applications for SIFTER Screening Strategies.

It is herein disclosed that applications of SIFTER strategies are limited only by the prerequisites which are proposed herein. A number of existing and developing technologies may be ideally suited for screening using SIFTER-based strategies. Examples include the development of phage-display libraries of the *B. thuringiensis* toxins for the selection of mutants with altered specificities (Marzari et al., 1997, Kasman et al., 1998) and the in situ expression of recombinant peptides by symbionts of *Rhodnius prolixus* which reduce *Trypanosoma cruzi* transmission (Durvasula et al., 1997). Recombinant insect viruses show particular promise (Matsubara et al., 1996, Olson et al., 1996) and may allow screening for genes from pathogen-refractory arthropod lines in otherwise identical susceptible lines. Conversely, it might also be possible to screen for genes encoding receptors for pathogen invasion in otherwise incompetent arthropod vectors. Recent advances in insect virus technology (Matsubara et al., 1996, Ernst et al., 1998, Granziero et al., 1997) suggest that it may soon be possible to display, select and screen libraries in such nucleic acid vectors. More simply, screening panels of microorganisms, rather than genes, for new insecticidal isolates might be useful to accelerate the search for alternatives to *B. thuringiensis* (Bowen et al., 1998).

In conclusion, SIFTER-based strategies extend and accelerate the ongoing search for new (Bowen et al., 1998) and modified (Marzari et al., 1997, Kasman et al., 1998) biomolecules with activity against insects and other arthropods of economic and medical importance. SIFTER screening may be particularly useful in the development of vaccines for the control of arthropods and the pathogens they transmit (Jacobs-Lorena & Lemos, 1995, Willadsen & Billingsley, 1996).

The following references were cited herein:

Alger, N. E. & Cabrera, E. J. (1972) *J Econ Entomol* 65: 165–168.
Almeida, A. P. G. & Billingsley, P. F. (1998) *Int J Parasitol* 28: 1721–1731.
Billingsley, P. F. (1994) *Trans Roy Soc Trop Med Hyg* 88: 136–140.
Bowen, D., et al. (1998) *Science* 280: 2129–2132.
Cai, X. & Garen, A. (1995) *Proc Natl Acad Sci USA* 92: 6537–6541.
do Rosario, V. E., et al. (1989) *Trans Royal Soc Trop Med Hyg* 1989: 305–307.
Durvasula, R. V., et al. (1997) *Proc Natl Acad Sci USA* 94: 3274–3278.
Ernst, W., et al. (1998) *Nucleic Acids Res* 26: 1718–23.
Friend, W. G. & Smith, J. J. B. (1982) *J Insect Physiol* 28: 371–376.
Galun, R., et al. (1985) *Physiol Entomol* 10: 275–281.
Granziero, L., et al. (1997) *J Immunol Methods* 203: 131–9.
Hatfield, P. R. (1988) *Med Vet Entomol* 2: 331–338.
Higgs, S., et al. (1996) *Biotechniques* 21: 660–664.
Jacobs-Lorena, M. & Lemos, F. J. A. (1995) *Parasitol Today* 11: 144–147.
Kasman, L. M., et al. (1998) *Appl Environ Microbiol* 64: 2995–3003.
King, R. W., et al. (1997) *Science* 277: 973–974.
Knols, B. G. (1996) *Odour-mediated host-seeking behaviour of the Afro-tropical malaria vector Anopheles gambiae Giles*, CIP Data Koninklijke Bibliotheek, Den Haag.
Lackie, A. M. & Gavin, S. (1989) *Med Vet Entomol* 3: 225–230.
Lal, A. A., et al. (1994) *Infec Immun* 62: 316–318.
Marshall, A. (1998) *Nature Biotechnol* 16: 530–533.
Marzari, R., et al. (1997) *FEBS Lett* 411: 27–31.
Matsubara, T., et al. (1996) *Proc Natl Acad Sci USA* 93: 6181–6185.
McCafferty, J., et al. (1994) *Appl Biochem Biotechnol* 47: 157–173.
McCafferty, J. & Johnson, K. S. (1996) *Phage display of peptides and proteins: A laboratory manual* (Eds, Kay, B. K., Winter, J. & McCafferty, J.) Academic Press, San Diego, pp. 79–112.
Noden, B. H., et al. (1995) *J Amer Mosquito Contr Assoc* 11: 45–49.
Noden, B. M., et al. (1994) *Acta Tropica* 58: 13–19.
Olson, K. E., et al. (1996) *Science* 272: 884–886.
Oparka, K. J., et al. (1997) *Nature* 388: 401–402.
Ponnudurai, T., et al. (1989) *Parasitology* 98: 165–173.
Ramasamy, M. S. & Ramasamy, R. (1990) *Med Vet Entomol* 4: 161–166.
Ramasamy, M. S., et al. (1988) *Med Vet Entomol* 2: 87–93.
Ramasamy, M. S., et al. (1990) *Med Vet Entomol* 4: 49–55.
Ramasamy, M. S., et al. (1992) *J Med Entomol* 29: 934–938.
Ramasamy, R., et al. (1997) *Biochim Biophys Acta* 1361: 114–22.
Srikrishnaraj, K. A., et al. (1995) *Med Vet Entomol* 9: 353–357.
Stewart, C. N. J., et al. (1996) *Plant Physiol* 112: 121–129.
Straif, S. C., et al. (1998) *J Med Entomol* 35: 222–226.
Sutherland, G. B. & Ewen, A. B. (1974) *J Insect Physiol* 20: 655–660.

VanWye, J. D. & Haldar, K (1997) *Mol Biochem Parasitol* 87: 225–229.

Vaughan, J. A. & Azad, A. F. (1988) *J Med Entomol* 25: 472–474.

Vaughan, J. A., et al. (1988) *Exp Parasitol* 66: 171–182.

Vaughan, T. J., et al. (1998) *Nature Biotechnol* 16: 535–539.

Vaughan, T. J., et al. (1996) *Nature Biotechnol* 14: 309–314.

Willadsen, P. & Billingsley, P. F. (1996) Immune intervention against blood-feeding insects. *Biology of the Insect Midgut* (Eds, Lehane, M. J. & Billingsley, P. F.) Chapman & Hall, London, pp. 323–344.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening a nucleic acid library for a biomolecule that kills an arthropod, comprising the steps of:
   (a) feeding an array of elements to a population of arthropods, wherein each element of said array contains a clone or mixture of clones of said nucleic acid library, wherein individual arthropod mainly feeds on a single element but has the opportunity to feed upon any element in the array;
   (b) isolating dead arthropods from said population of arthropods after feeding on said array;
   (c) preparing midgut samples from said dead arthropods; and
   (d) recovering a clone or mixture of clones of said nucleic acid library from said midgut samples of said dead arthropods, wherein said clone or mixture of clones encode a biomolecule that kills said arthropod.

2. The method of claim 1, further comprising the step of:
   performing iterative cycles of steps (a), (b), (c) and (d) until a single clone of said nucleic acid library is isolated.

3. The method of claim 1, wherein step (a) is preceded by a step comprising:
   enriching said nucleic acid library for nucleic acids that encode midgut-specific biomolecules.

4. The method of claim 1, wherein said arthropod is a mosquito.

5. The method of claim 4, wherein said mosquito is *Anopheles gambiae*.

6. The method of claim 1, wherein said nucleic acid library is selected from the group consisting of an expression library, a library of nucleic acid fragments, genomes of naturally-occuring microbes, genomes of naturally-occuring viruses, genomes of genetically modifed microbes and genomes of genetically modifed viruses.

7. The method of claim 6, wherein said expression library is selected from the group consisting of a phagemid library, a phage-display library, a eukaryotic nucleic acid vector-based expression library, a prokaryotic nucleic acid vector-based expression library and a library of nucleic acid fragments with the potential to exhibit a phenotype in an arthropod.

8. The method of claim 1, wherein said clone of said nucleic acid library encodes a biomolecule selected from the group consisting of a toxin, a monoclonal antibody, a polyclonal antibody, a single-chain antibody, a naturally occurring microbe, products encoded by pathogen-refractory genes, receptors for pathogen invasion and a product encoded by a gene with a potential to kill said arthropod.

9. A method of screening a nucleic acid library for a biomolecule that kills the malaria vector mosquito *Anopheles gambiae*, comprising the steps of:
   (a) feeding an array of elements to a population of *Anopheles gambiae*, wherein each element of said array contains a clone or mixture of clones of said nucleic acid library, wherein individual *Anopheles gambiae* mainly feeds on a single element but has the opportunity to feed upon any element in the array;
   (b) isolating dead *Anopheles gambiae* from s aid population of *Anopheles gambiae* after feeding on said array;
   (c) preparing midgut samples from said dead *Anopheles gambiae*; and
   (d) recovering a clone or mixture of clones of said nucleic acid library from said midgut samples of said dead *Anopheles gambiae*, wherein said clone or mixture of clones encode a biomolecule that kills *Anopheles gambiae*.

10. The method of claim 9, further comprising the step of:
    performing iterative cycles of steps (a), (b), (c) and (d) until a single clone of said nucleic acid library is isolated.

11. The method of claim 9, wherein step (a) is preceded by a step comprising:
    enriching said nucleic acid library for nucleic acids that encode midgut-specific biomolecules.

12. The method of claim 9, wherein said nucleic acid library is selected from the group consisting of an expression library, a library of nucleic acid fragments, genomes of naturally-occuring microbes, genomes of naturally-occuring viruses, genomes of genetically modifed microbes and genomes of genetically modifed viruses.

13. The method of claim 12, wherein said expression library is selected from the group consisting of a phagemid library, a phage-display library, a eukaryotic nucleic acid vector-based expression library, a prokaryotic nucleic acid vector-based expression library and a library of nucleic acid fragments with the potential to exhibit a phenotype in an arthropod.

14. The method of claim 9, wherein clone of said nucleic acid library encodes biomolecule selected from the group consisting of a toxin, a monoclonal antibody, a polyclonal antibody, a single-chain antibody, a naturally occurring microbe, products encoded by pathogen-refractory genes, receptors for pathogen invasion and a product encoded by a gene with a potential to kill *Anopheles gambiae*.

* * * * *

UNITED STATES PATENT AND TRADEMARK OFFICE
CERTIFICATE OF CORRECTION

PATENT NO.    : 6,472,150 B1
DATED         : October 29, 2002
INVENTOR(S)   : Gerry F. Killeen, Brian D. Foy and John C. Beier It is certified that error appears in the above-identified patent and that said Letters Patent is hereby corrected as shown below:

<u>Title page,</u>
Item [75], "Brian D. Fox" should read -- Brian D. Foy --.

Signed and Sealed this

Eleventh Day of February, 2003

JAMES E. ROGAN
*Director of the United States Patent and Trademark Office*